United States Patent [19]

Mayer

[11] Patent Number: 5,591,898
[45] Date of Patent: Jan. 7, 1997

[54] METHOD FOR MEASURING MATERIAL PERMEABILITY CHARACTERISTICS

[75] Inventor: William N. Mayer, White Bear Lake, Minn.

[73] Assignee: Modern Controls, Inc., Minneapolis, Minn.

[21] Appl. No.: 542,318

[22] Filed: Oct. 12, 1995

[51] Int. Cl.$^6$ .................................................. G01N 15/08
[52] U.S. Cl. .................................................................. 73/38
[58] Field of Search .......................... 73/38, 19.01, 37, 73/866

[56] References Cited

U.S. PATENT DOCUMENTS

| | | | |
|---|---|---|---|
| 3,498,110 | 3/1970 | Brun | 73/38 |
| 3,590,634 | 7/1971 | Pasternak et al. | 73/38 X |
| 3,604,246 | 9/1971 | Toren | 73/38 |
| 3,618,361 | 11/1971 | Stephens et al. | 73/38 |
| 3,926,561 | 12/1975 | Lucero | 73/38 X |
| 4,464,927 | 8/1984 | Reid | 73/38 |
| 4,656,865 | 4/1987 | Callon | 73/38 |
| 4,660,411 | 4/1987 | Reid | 73/38 |
| 5,513,515 | 5/1996 | Mayer | 73/38 |

FOREIGN PATENT DOCUMENTS

| | | | |
|---|---|---|---|
| 119433 | 5/1987 | Japan | 73/38 |
| 1755120 | 8/1992 | U.S.S.R. | 73/38 |

OTHER PUBLICATIONS

Article: "Leakage and Permeation: Theory and Practical Applications," Mary A. Amini & Darrell R. Morrow, pp. 20–26.

Article: "Measuring Gas Permeability of Plastic Films," Walter Soroka, *Canadian Packaging*, Aug. 1979, pp. 17 & 19.

Article: "Permeation Speeds Tests, Aids Choice of Exact Material," Murray, Dorschner, *Package Engineering*, Mar. 1983, pp. 76–80.

Article: "Plastics in Packaging: Gas and Vapor Permeation," Ravi Talwar, Ph.D., based on a paper presented at the Plastics in Packaging seminar sponsored by the Plastics Institute of America, pp. 29–32 & 49–53.

Article: "Permeability of Plastics," Carl W. Hall, Technical/Engineering Methods, Research, Testing, Nov. 1973, pp. 53–57.

Article: "Factors Affecting the Oxygen Barrier of Vinylidene Chloride–Vinyl Chloride Copolymers," Phillip T. Delassus, Saran and Converted Products Research, The Dow Chemical Company, Midland, Michigan 48640, Plastics in Packaging, Nov. 1978, pp. 78–82.

*Primary Examiner*—Hezron E. Williams
*Assistant Examiner*—Daniel S. Larkin
*Attorney, Agent, or Firm*—Palmatier, Sjoquist, Helget & Voigt, P.A.

[57] ABSTRACT

A method for measuring the permeability of a gas through a material, wherein the steps include exposing the material to the gas to be measured and measuring the outgassing characteristics of the material over increments of time to develop exponential expressions representative of the measured amounts and solving the exponential expressions for the diffusion coefficient D and the solubility coefficient S; and then calculating the permeability of the material by forming the product of the diffusion coefficient D and the solubility coefficient S.

5 Claims, 3 Drawing Sheets

METHOD FOR MEASURING MATERIAL PERMEABILITY CHARACTERISTICS

BACKGROUND OF THE INVENTION

The present invention relates to a method and apparatus for measuring characteristics of materials relating to the permeability of the material. More particularly, the invention relates specifically to a method for measuring the diffusion coefficient, the solubility coefficient, and the permeability coefficient of a sample barrier material.

Certain apparatus for measuring the oxygen flow rate through membrane barrier materials are known in the prior art. For example, U.S. Pat. No. 3,618,361, issued Nov. 9, 1971, discloses an early system for measuring the gas permeability of a film. Similarly, U.S. Pat. No. 3,590,634 issued Jul. 6, 1971, discloses another instrument for measuring permeation rates through a membrane U.S. Pat. No. 4,464,927 issued Aug. 14, 1984, discloses an apparatus for measuring gas transmission through films in multiple test cells. All of these devices operate in conjunction with an oxygen detector which typically provides an electrochemical transformation in response to the presence of oxygen. One such oxygen detector is disclosed in U.S. Pat. No. 3,223,597, issued Dec. 14, 1965, and another form of oxygen detector is disclosed in U.S. Pat. No. 4,085,024, issued Apr. 18, 1978. All of these earlier patents, and a considerable number of more recent patents, utilize a test cell setup in conjunction with an oxygen detector to derive an electrical signal which is representative of the amount of oxygen within a given chamber of the test cell. A sample of the barrier material undergoing testing is typically clamped within the test cell to form two chambers, wherein one chamber is initially free of oxygen and filled with a neutral gas such as nitrogen, and the other chamber is initially saturated with oxygen. Before proceeding with these initial conditions, it is first necessary to outgas all oxygen from the material sample undergoing tests. Outgassing is accomplished by flowing a neutral gas such as nitrogen through both chambers described above, monitoring the test gas for oxygen content until it appears that the oxygen content has become depleted to zero, or near zero, and then proceeding with the initial Conditions described above. The test process requires that the neutral test gas flow be monitored until the oxygen concentration in the test gas reaches a steady state level, which can require many hours of operation. In general, the amount of time required for such a test is directly related to the permeability coefficient of the material and inversely related to the material thickness. The permeability coefficient is directly related to temperature and, to a lesser extent, pressure. The objective of tests of this type is to measure the amount of oxygen which permeates through the test membrane under steady state conditions, and the oxygen measurements are typically made by devices which are disclosed in the foregoing prior art patents.

The large majority of permeation measurements now being made are in terms of the amount of gas permeating a given sample. This may be a container or an essentially flat sample. The answers are given in terms of the volume or weight of a gas permeating the sample in a given time. In the case of a container, this becomes the volume or weight of gas per time per container. In the case of a flat sample, it is the volume or weight of a gas per time per unit area. These answers are obtained and refer to the conditions of the test. In a formal way, these are not permeation values but are transmission rate values for that gas, through that sample under the specific test conditions.

For example:
Sample—10 mil flat film (PET)
Transmission Rate for $O_2$:

$$7.5 \frac{cc}{M^2 \cdot day} \text{ at one atmosphere}$$

Pressure, 30° C. and less than 5% RH.

The definition of the permeation rate for a film (in the same units) is referred to a standard temperature and pressure (STP) (760 mm Hg, 0° C.) for a 1 mil film. The amount of gas being transferred is roughly inversely proportional to the film thickness. At the test conditions, a 1 mil film would then transmit ten times as much $O_2$ as a 10 mil sample.

$$\text{Transmission Rate (1 mil)} = 75 \frac{cc}{M^2 \cdot day}$$

Correction to 0° C. would then result in the formally defined permeation rate.

Basically, the permeation of gas through a material results from the inherent physical characteristics of the material. These characteristics have been formally defined in all of the literature in the field for the last 30 years. These characteristics are: the solubility of the material to the gas of interest in the material and the rate of diffusion of the gas through the material. The solubility coefficient "S" defines the volume of gas which will dissolve in a like volume of the material; i.e.$(cm^3/cm^3)$; and the diffusion coefficient "D" denotes the rate at which the gas moves through the material; i.e. $(cm^2/sec)$. The product of the solubility coefficient "S" and the diffusion coefficient "D" is called the permeability coefficient "P"; and in this case, the units are $[(cm^3/sec)/(cm^2/cm)]$, interpreted as "cubic centimeters of gas per square centimeter of area per second, per centimeter of thickness of material." The permeability coefficient "P" is related to the actual material permeability $P_{actual}$; i.e., the transmission rate of the gas through a given sample of material; by a simple conversion factor, which converts "cubic centimeters per second per centimeter of thickness" to a standard in terms of "cubic centimeters per day per 10 millimeter of thickness and per square meter of area," wherein the conversion factor is $$P_{actual} = P/(2.94 \times 10^{-12}).$$

As noted above, this information is well known. All aspects have been reviewed for years in the literature on the subject of permeation. The background is necessary, however, to follow the new method of measurement of the transmission of gas through a material.

A theoretical analysis of absorption and description of gases into materials is given by J. Frank in his book *Mathematics of Diffusion,* 2nd Edition, Clarendon Press, Oxford, England (1975).

The most used present method of measurement today is termed isostatic. This refers to the case in which a sample is mounted in such a way that one side of the sample is exposed to the gas of interest. The other side is isolated at zero, or extremely low levels, of that gas. In this way, the gas permeating the sample can be measured as a function of time.

Usually the film is first outgassed by flowing a neutral gas over both sides of the sample. Then the permeant gas is made to flow on one side, while the neutral gas flows on the other side through a sensor which is responsive to very small concentrations of the permeant gas. The final answer is obtained by waiting until the permeant gas concentration on the sensor side reaches a steady state value which is indicative of a steady-state permeation through the material sample. Typically, the time required for waiting until a steady-state permeation condition exists is usually quite long for even moderately good barriers. For instance, a PET film, 10 mil ($10^{-2}$ inches) thick, at 30° C., has a permeation (transmission) value of approximately 7.5($cm^3/M^2$)/day; i.e., 7.5 cubic centimeters per meter square per day. Many barriers today yield permeation measurements less than one-tenth of this value. With such materials, the preparatory outgassing of a 10 mil sample will take about 21 hours, and the permeation measurement requires about 29 hours.

It would be extremely desirable if the amount of time required for making valid permeation measurements could be significantly reduced. The equipment required for making such measurements is fairly expensive and complex; and therefore, the measurement of a single sample of material can require the exclusive use of a station having such equipment for a period of several days. If a significant number of samples require measurement, the number of test stations set up with the necessary equipment for such measurements must be multiplied to fit the testing schedule. Therefore, any modification through the overall process which can be made by way of shortening the total test time will be of great advantage and significance in the field.

SUMMARY OF THE INVENTION

The present invention comprises a method and apparatus for measuring the diffusion coefficient and solubility coefficient of barrier materials in a relatively short period of time which allows the permeability, or transmission rate, of a sample gas flowing through the material to be calculated in a radically shortened period of time as compared to the prior art techniques which are available. The method is carried out by the same equipment as was formerly used for such measurements, but the results are achieved by measuring the outgassing characteristics of the material rather than subjecting the material to the two stages of outgassing and then measuring permeability. The method is derived from the recognition that the permeability characteristics of the material can be predictably determined by analysis of the complex, non-linear, behavior of the material during the outgassing process, and the recognition that the permeability of the material is directly related to the material's outgassing characteristics. Briefly, the method steps comprise outgassing a gas-saturated material and observing the exponential rate of decay of the outgassed gas, for instance oxygen, over a predetermined interval of time. It has been found empirically that the outgassing curve for a material can be closely approximated by the sum of two exponentials, and points along the outgassing curve for a given material can be measured, to yield a measurement of the material's diffusion coefficient "D" and solubility coefficient "S." Once these coefficients are determined, the gas transmission rate through the material is readily derived mathematically.

Application of the present method to known materials will result in an overall decrease in the required measurement time interval by a factor of about 40 and will result in a sensitivity improvement of about a factor of 4 when compared with the existing methods in the prior art.

Accordingly, it is a principal object and advantage of the present invention to provide a measure of the permeability of a material and, therefore, the gas transmission rate through the material in a much shorter time interval than is known in the prior art.

It is another object and advantage of the present invention to provide such a measurement with a much higher degree of sensitivity than is possible in the prior art.

Other and further objects and advantages of the invention will become apparent from the following specification and claims and with reference to the appended drawings.

DETAILED DESCRIPTION OF THE DRAWINGS

DETAILED DESCRIPTION OF THE PREFERRED EMBODIMENT

Figure 1:
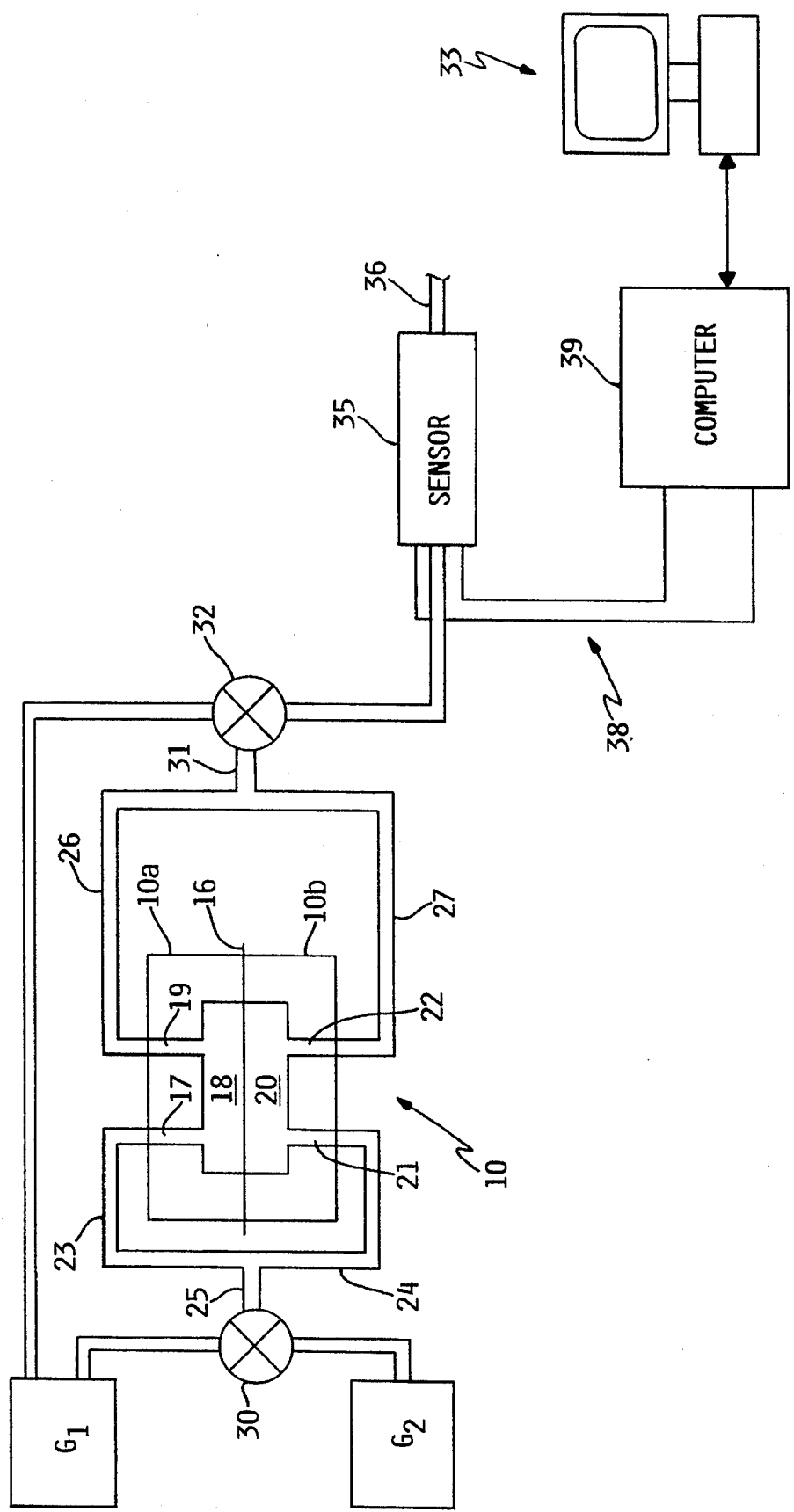
FIG. 1 shows a diagrammatic representation of the apparatus for performing the inventive method.

Referring first to FIG. 1 of the drawings, there is shown a diagrammatic representation of an apparatus which can be used for performing the method of the present invention. A measurement cell 10 of the type typically used for gas transmission and permeability measurements in the prior art is shown. Cell 10 has two separable halves 10a and 10b which may be clamped together over a material sample 16, thereby creating two interior chambers 18 and 20 separated by the material sample 16. A pair of gas passages 17, 19 open into chamber 18, and a pair of gas passages 21, 22 open into chamber 20. Conduits 23, 24 are respectively connected to passages 17, 21 and are joined together into a single conduit 25. Conduit 25 is connected to a two-way valve 30 which is connected to a first gas source G1 and a second gas source G2 in a manner that permits either gas source G1 or G2, but not both simultaneously, to be connected to conduit 25. Conduits 26, 27 are respectively connected to passages 19, 22 and are joined together into a single conduit 31. Conduit 31 is connected to a two-way valve 32, which is connected to gas source G1 and sensor 35 in a manner which permits conduit 31 to be connected to either gas source G1 or sensor 35, but not both simultaneously. Sensor 35 has an exhaust conduit 36 which may exhaust to atmosphere.

Sensor 35 may be a sensor of the type described in the prior art described herein, or another type of sensor which is capable of detecting small concentrations of a test gas carried in a flow of a neutral gas. Sensor 35 has electrical output lines 38 which are connected to a computer processor 39, after conversion of the signals to digital values through an analog-to-digital voltage converter, to provide a signal to computer processor 39 which is proportional to the detected concentrations of test gas flowing through sensor 35.

Computer processor 39 may be connected to a visual display device 33, such as a CRT workstation, which is capable of displaying a graphical or numerical representation of the signals from sensor 35, and of the measured and calculated values of diffusion coefficient, solubility coefficient, and permeability or transmission rate, all as relates to the material sample 16 and the test gas. Computer processor 39 may be any of a number of commercially-available computer processors comprising a general purpose digital computer having internal memory and processing capability for interpreting computer programs. The method steps described herein which relate to the calculation of certain values may be implemented by the computer processor 39 via a software program which may be prepared by one having ordinary skill in the art of computer programming. In this art, it is well known to develop computer programs for solving complex mathematical problems, including programs for solving all of the mathematical steps which are recited or implied in the following description of the method.

In operation, the measurement cell 10 can be used both for saturating a material sample 16 with a test gas G1 and for conducting the necessary measurements via sensor 35; alternatively, a separate chamber or other location can be used for saturating the material sample 16 with a test gas G1. If the measurement cell 10 is used for saturating the material sample 16 with a test gas G1, valve 30 is operated to connect conduit 25 to the gas source G1, and valve 32 is operated to connect conduit 31 back to gas source G1. The gas from gas source G1 is then allowed to flow through both chambers 18 and 20 for a sufficiently long time to ensure that the material sample 16 has become thoroughly exposed to the gas from source G1, to saturate the material sample 16 with the gas from gas source G1. The length of time required for saturation to occur can be empirically determined, and no external measurements need be made during this time. After the material sample 16 has become saturated with the test gas, the measurement process can begin.

A preliminary outgassing step must be performed before the measurement process can take place to ensure that no test gas is contained in chambers 18 and 20. This preliminary outgassing step is accomplished by connecting both chambers 18, 20 in the measurement cell 10 to a neutral gas supply G2 and flowing the neutral gas through both chambers 18 and 20 for several minutes. The outgassing step may be measured by the gas sensor 35, which will detect a sharply reduced quantity of test gas as the neutral gas flows through both sides of the measurement cell 10 followed by a gradual increase in the concentration of test gas as the material sample 16 begins outgassing the test gas which it has absorbed. At the beginning of this outgassing process, the measurements can begin by recording the electrical signals from sensor 35 at discrete time intervals. The measured signals are converted to digital values and are stored in computer processor 35, correlated to the respective times when each of the measurements were recorded. The data so recorded and stored will follow a general non-linear exponential decay curve which can be subsequently plotted and displayed on display device 33 as a function of time.

Figure 2:
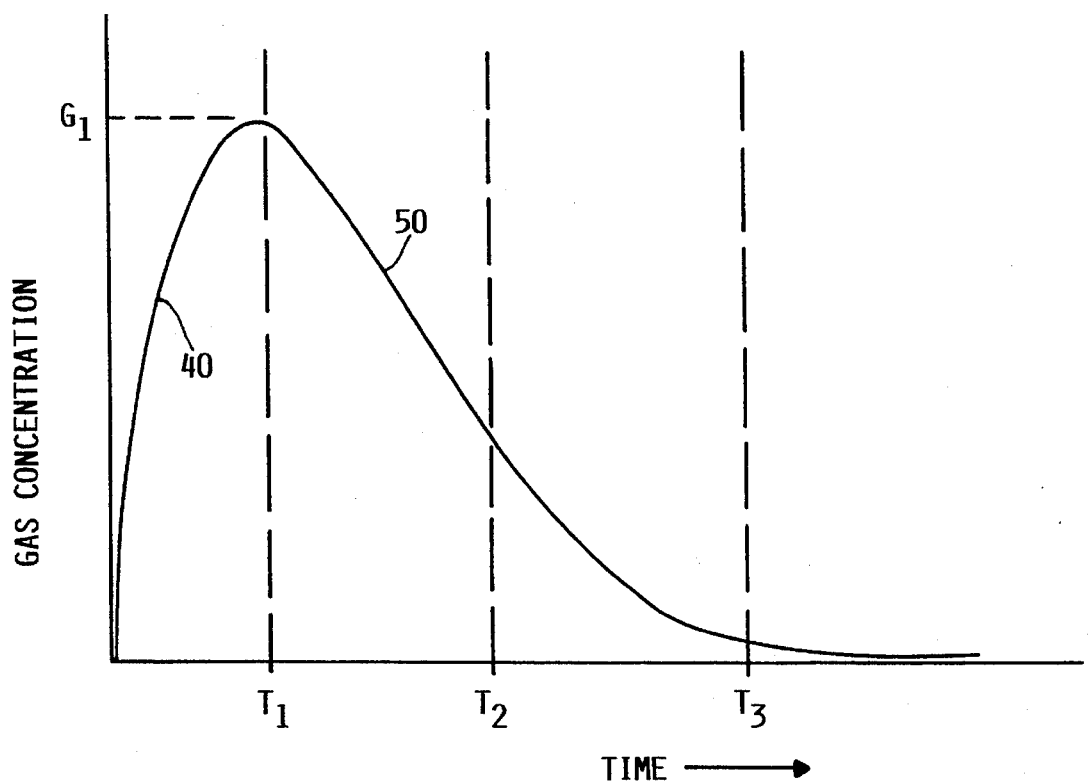
FIG. 2 shows the time-related curve for measuring gas concentration.

FIG. 2 shows a time curve to illustrate both the preliminary outgassing step and the outgassing measurement step for a typical measurement process. The preliminary outgassing step continues until time T1, which is determined by monitoring the gas concentration level measured by the sensor 35, and waiting until the measured concentration level has begun dropping after a rapidly rising initial series of measurements. This is shown by curve portion 40 in FIG. 2, which is a rapidly rising non-linear curve. The rising non-linear portion 40 is measurable by the apparatus illustrated in FIG. 1, and the particular shape of this curve portion is thought to be governed by many effects, including the relatively slow response of the sensor 35 to the gas initially passing through the sensor. At time T1 the sensor 35 response stabilizes and the neutral gas flow through chambers 18, 20 begins picking up the test gas which is being outgassed from material sample 16. Thereafter, the sensor 35 continues to monitor test gas concentration in the neutral gas flowing through sensor 35, which follows a decaying curve. The outgassing characteristics may be periodically measured until time T3, although sufficient data will probably be recorded well before time T2 to permit a complete determination of the material characteristics according to the present invention.

In the prior art, it typically required about 20 hours for the outgassing step to time T3 to be performed and about another 30 hours for the permeability measurement step to be performed. According to the teachings of the present invention, the necessary data may be collected in advance of time T2 to permit the measurement process to be completed in less than two hours.

The present invention, and the improved results derived therefrom, result from the realization that the permeation characteristics of a material sample which lead to a measurement and calculation of the gas transmission rates through the material are the same characteristics that govern the outgassing characteristics of the material. Further, it has been discovered that the outgassing characteristics of a material can be very closely approximated by an exponential equation which is the sum of two exponential terms and that when these exponential terms are properly defined the measured outgassing response curve can be predicted. The observation and analysis of this phenomena has led to the development of the present invention which will be described hereinafter.

Initially, it is recognized that the outgassing of a material is controlled by the diffusion coefficient and the solubility coefficient of the material; and if outgassing is observed only on one side of a material film or membrane, it must be realized that the outgassing measurement is made for only one-half the thickness of the membrane material; i.e., it must be assumed that the other side of the membrane is outgassing at the same rate. It has been empirically determined that the outgassing follows an exponential curve, or the sum of a number of exponential curves, which relate to the diffusion coefficient "D" and the solubility coefficient "S" of the material. By using curve fitting techniques it is possible to solve for the exponential curves and to calculate a value for the permeability of the material. It has been found empirically that the outgassing curve 50 of FIG. 2 can be closely approximated by the sum of two exponential curves of the form $Ke^{-xt}$.

Figure 3:
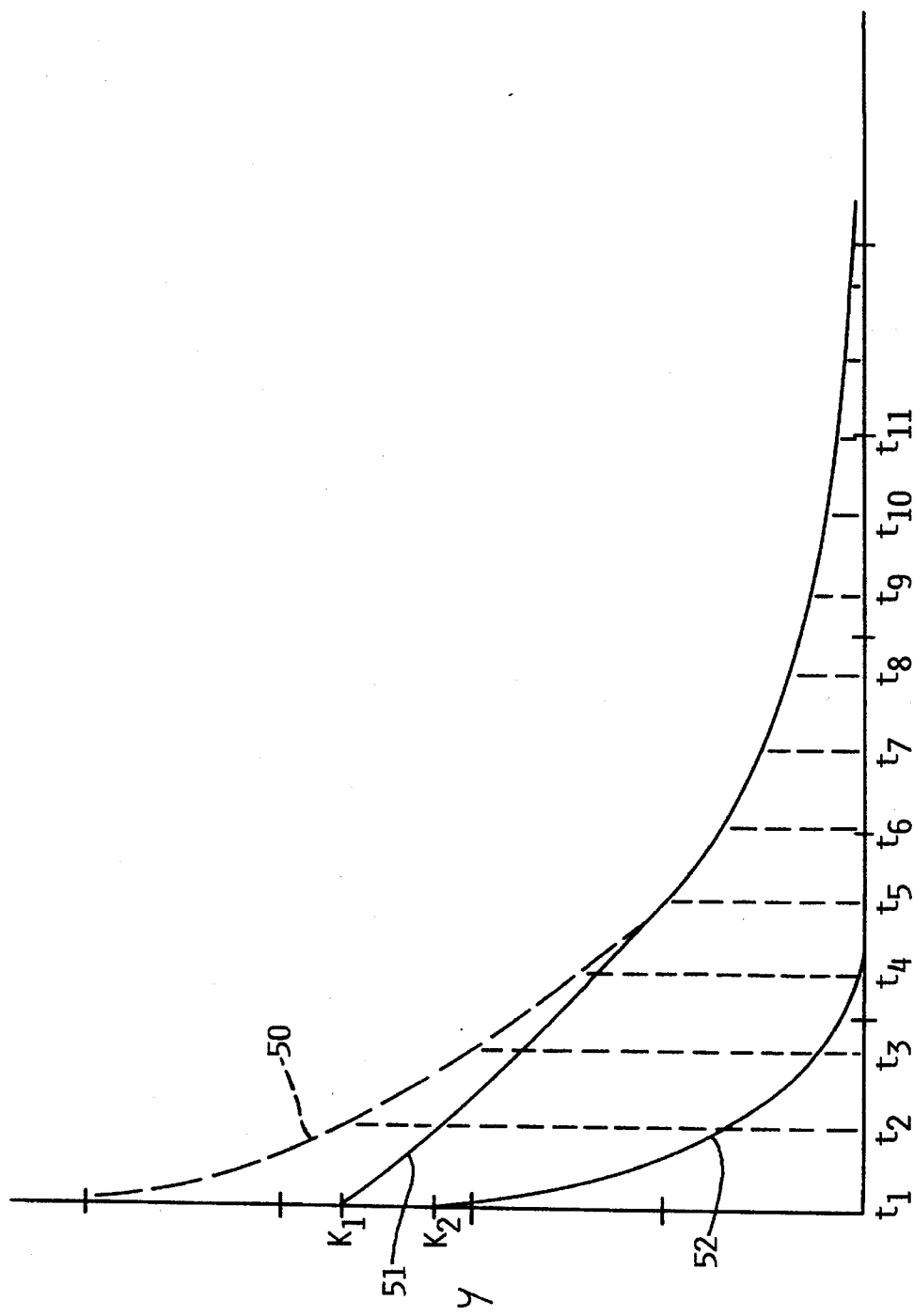
FIG. 3 shows an expanded view of a portion of the curve of FIG. 2.

FIG. 3 shows an expanded portion of the curve of FIG. 2, illustrating the outgassing curve 50 and extrapolating it back to a zero time scale ($t_1=0$). In particular, the outgassing curve 50 can be empirically shown to be the sum of the exponential curves 51 and 52, where curve 51 is in the form $$y_1(t)=K_1e^{-at};$$

and curve 52 is in the form $$Y_2(t)=K_2e^{-bt};$$

so that curve 50 can be represented by the equation $$y(t)=y_1(t)+y_2(t)=K_1e^{-at}+K_2e^{-bt}.$$

The value of the exponents "a" and "B" can be determined empirically by a curve fitting process applied to actual measurement results. After time $t_4$ (see FIG. 3) the second term in the foregoing equation becomes small enough to be ignored, and the function reduces essentially to $y(t)=K_1e^{-at}$.

Assuming the curve 50 behaves as an exponential curve according to the foregoing equation after time $t_4$, the values for $K_1$ and the exponent "a" must be determined. A characteristic of any exponential curve is that, for any particular time increment $t_i$, the ratio of the value of y(t) taken at the beginning and end of the time increment is a constant; i.e., if a time increment $t_i$ is chosen as the time between time $t_4$ and time $t_5$, or between time $t_5$ and time $t_6$ (assuming these are equal time increments), then the ratio $[y(t_4)/y(t_5)]$ equals the ratio $[Y(t_5)/Y(t_6)]$, etc. Because this is a true and correct characteristic of exponential curves, it then becomes possible to measure the y(t) curve at equal time increments $_i$ and to calculate the actual measured ratios described above until a point is reached along the curve where the ratios become equal (at a ratio value $R_1$); at that point it can be surmised that the measured y(t) curve is behaving as a single exponential expression of the form $y(t)=K_1e^{-at}$. Furthermore, if the measured value of the ratio at that point is $R_1$, then $R_1=e^{-at}$, where $t=t_i$; taking the logarithmic value of this equation leads to $$Ln(R_1)=-at_i \text{ or } -a=Ln(R_1)/t_i.$$

The value for $K_1$ can be found by extrapolating the curve $y_1(t)=K_1e^{-at}$ back to zero time, where $y(t_4)/R_1^4=K_1$, since there are 4 time increments $t_i$ from $t_4-t_5$ back to zero time (see FIG. 3).

The foregoing solution of the equation $y_1(t)=K_1e^{-at}$ yields values for $K_1$ and the exponent "a." We conclude that the exponential decay of this equation must be governed by the rate of diffusion of gas through the material sample; i.e., the exponent "a" is related to the diffusion coefficient D. By testing known material samples it is empirically determined that the exponent "a" is proportional to both the diffusion coefficient D and one-half the thickness of the material sample "l" according to the following equation:

$$a=M(D/l^2); \text{ where } M=2.4.$$

The constant "M" may be related to the particular material composition, but experimentation with known plastic film materials leads to the empirical determination of the value of M=2.4. It is possible that the value for M may have to be varied for certain materials which have not yet been tested, but in such case the teachings herein will permit a new value to be selected for this constant. Solving the foregoing equation for the diffusion coefficient D:

$$D=(l^2)(Ln\ R_1)/2.4(t_i).$$

Therefore, the foregoing description shows that the diffusion coefficient D for a material under test and measurement with the apparatus shown in FIG. 1 can be determined during an early portion of the outgassing curve measured for such material. Typically, this determination may be made many hours earlier than has previously been possible with prior art techniques.

Having determined the diffusion coefficient D for the material sample there remains the task of determining the solubility coefficient S for the same material, in order to use these values to calculate the permeability coefficient P, according to the known formula P=S·D. The solubility coefficient is a measure of the ability of the material sample to absorb the gas under test, and may be expressed by the ratio of the total amount of gas outgassed from the material sample to the volume of the material sample itself; i.e., $S=V_{tot}/V_{sample}$. The volume of the material sample is readily determined as the product of the material sample area and the material sample thickness. The total volume of test gas outgassed from the material sample can be approximated as the area under the curve 50 of FIG. 3, which requires an integration of the equation $y(t)=K_1e^{-at}+K_2e^{-bt}$.

The first term in this equation was determined by the description earlier, and the second term can be found by subtracting the $y_1(t)$ curve from the measured curve of FIG. 2, assuming the zero point of the curve begins at time $T_1$; i.e., time $t_1$ of FIG. 3 corresponds to zero and to time $T_1$ of FIG. 2. By making a point-by-point subtraction of curve 51 from curve 50 of FIG. 3, the curve 52 maybe plotted as a representation of the equation $y_2(t)=K_2e^{-bt}$.

The values of the constant $K_2$ and the exponent "b" can be determined in the same manner as was described earlier with respect to the first expression in the y(t) equation. The $Y_2(t)$ curve can be extrapolated to zero to determine the constant $K_2$, and the same sort of time increment ratios can be measured to establish a ratio $R_2$ which represents a constant decay ratio for the $y_2(t)$ curve. Therefore, the exponent "B" value can be established as $b=Ln(R_2)/t_i$, where $t_i$ is the time increment previously established. Thereafter, integrating the expression $K_1e^{-at}+K_2e^{-bt}$ from time t=0 to time t=∞, the total volume $V_{tot}$ of gas outgassed from the material sample is determined. The solubility coefficient S is then determined by:

$$S=V_{tot}/V_{sample}.$$

The permeability coefficient P can then be calculated as the product of S and D, and the actual permeability of the material sample, or its gas transmission rate, can be calculated by applying the conversion factor described earlier herein.

In operation, the measurements to obtain the plotted curve 50 can be accomplished by the apparatus of FIG. 1, or by an equivalent gas sensor hookup, and the number of plotted samples of gas sensor readings can be constantly tested to determine the conditions for establishing the ratio $R_1$, whereupon no further data need be collected from the sensor 35 in order to practice the method described herein for determining the permeability or transmission rate of the material sample. In practice, the apparatus and method described herein permit this determination to be made in minutes rather than the many hours previously required for such determination.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. A method for measuring the permeability of a gas through a material, comprising the steps of:
   a) exposing the material to the gas to be measured;
   b) measuring the amount of said gas which is outgassed from said material over successive increments of time; and forming a curve plot which represents the outgassed amount (y) versus time;
   c) choosing a uniform time increment ($t_i$) and subdividing said curve plot into uniform time increments $t_i$;
   d) measuring the value of y at the beginning and end of each time increment $t_i$ and forming the ratio $R_1$ thereof, and continuing until the nth and (n+1) time increments $t_i$ when two subsequent ratios $R_1$ are substantially equal;
   e) forming an equation $y_1(t)=K_1e^{-at}$ wherein $K_1=y(tn)/R_1^n$ and $-a=Ln\ R_1/t_i$;
   f) plotting a second curve of the equation $y_1(t)=K_1e^{-at}$ and subtracting said second curve from said formed curve plot to produce a third curve of the equation $y_2(t)=K_2e^{-bt}$;
   g) measuring the value of $Y_2$ at the beginning and end of each uniform time increment t; of said second curve, and forming the ratio $R_2$ of the value of $Y_2$ at the beginning and end of a time increment $t_i$;

h) solving for $K_2$ by the equation $K_2 = y_2(tn)/R_2^n$ and solving for "B" by the equation $b = \text{Ln } R_2/t_i$;

i) calculating the diffusion coefficient "D" by the equation $D = a\, l^2/2.4$ and calculating the solubility coefficient "S" by the equation $S = [K_1/a + K_2/b]/V$ where "l" is one-half the thickness of said material and "V" is the volume of said material; and j) calculating the permeability "P" of said material by the equation $P = S \cdot D$.

2. A method for measuring the diffusion coefficient D of a material sample having a predetermined thickness by measuring the outgassing characteristics of said material sample and fitting the measured characteristics to a curve of the form $y(t) = K_1 e^{-at} + K_2 e^{-bt}$, comprising the steps of:

a) exposing the material sample to the gas to be measured;

b) enclosing the material sample in a sealed chamber having a passage to a gas detector of the type which generates an electrical output signal which is representative of the amount of gas detected over time;

c) forming a curve plot $y(t)$ of said electrical output signal as a function of time;

d) choosing an increment of time $(t_i)$ and measuring the value $y(t)$ of said curve at the beginning and end of each of said chosen time increments and forming the ratio of successive pairs of said values $y(t)$ until two successive ratios so formed are equal, ratio $R_1$, at the n and (n+1) time increments;

e) selecting an approximation for the $y(t)$ curve for the nth and subsequent time increments, whereby $y(t) = K_1 e^{-at}$, and the exponent value "a" is equal to $(M \cdot D)/l^2$, where M is an empirically determined constant, l is one-half the thickness of the material sample, and D is the diffusion coefficient of the material sample;

f) selecting the logarithmic value "$C_1$" of the ratio $R_1$ formed at the nth time increment;

g) setting the value of M equal to approximately 2.4; and h) calculating the diffusion coefficient D of said material sample by the equation $D = (C_1 \cdot l^2)/(2.4) t_i$.

3. The method of claim 2, further comprising the steps of calculating the solubility coefficient S of the material for the gas outgassed from said material sample, after the diffusion coefficient D has been determined by the steps of:

a) calculating the value $R_1^n$ and setting the constant $K_1$ equal to the value $y(t_n)/R_1^n$ and setting the exponent "a" equal to $C_1/t_i$, thereby determining the value of the expression $K_1 e^{-at}$;

b) subtracting the calculated expression $K_1 e^{-at}$ for all times "t" from the formed curve plot $y(t) = K_1 e^{-at} + K_2 e^{-bt}$ to yield the remaining curve plot for $K_2 e^{-bt}$;

c) choosing said increment of time $(t_i)$ and measuring the value $y(t)$ of said remaining curve plot at the beginning and end of each of said chosen time increments and forming the ratio of successive pairs of said values $y(t)$ until two successive ratios so formed are equal, ratio $R_2$, at the m and (m+1) time increments;

d) selecting the logarithmic value "$C_2$" of the ratio $R_2$ formed at the mth time increment;

e) calculating the value $R_2^m$, and setting the constant $K_2$ equal to the value $y(t_m)/R_2^m$, and setting the exponent "B" equal to $C_2/t_i$;

f) measuring the volume V of said material sample; and g) calculating the solubility coefficient S of the material for the gas outgassed from said material sample by the equation $S = [K_1/a + K_2/b]/V$.

4. The method of claim 3, further comprising the step of determining the permeability coefficient P of said material sample by forming the product of S and D, where $P = S \cdot D$.

5. An apparatus for measuring the diffusion coefficient D of a material by measuring the outgassing characteristics of the material, comprising:

a) a measurement cell having a sealable chamber for holding said material, said chamber having a vent passage extending to the exterior of the cell;

b) a gas sensor coupled to said vent passage for receiving gas from said chamber, said sensor having an electrical circuit output responsive to gas detected by said sensor;

c) a computer processor connected to said electrical circuit output; said processor having means for sampling signals from said circuit output at uniform time increments and converting said sampled signals into digital values; said processor further having means for forming the ratio of said digital values at the respective beginning and end of each of said time increments and for identifying the time increments (n, n+1) when two successive ratios $R_1$ are substantially equal; said processor further having means for constructing an exponential equation of the form $y_1(t) = K_1 e^{-at}$, where $K_1 = y_1(tn)/R_1^n$ and $a = (\text{Ln } R_1)/t_i$; said processor further having means for calculating the diffusion coefficient D by the equation $D = a\, l^2/2.4$, where l is one-half the material thickness; and d) a graphic display having means for displaying the equation $y_1(t) = K_1 e^{-at}$ and means for displaying the value D.

* * * * *

UNITED STATES PATENT AND TRADEMARK OFFICE
CERTIFICATE OF CORRECTION

PATENT NO.   :  5,591,898
DATED        :  January 7, 1997
INVENTOR(S)  :  William N. Mayer It is certified that error appears in the above-indentified patent and that said Letters Patent is hereby corrected as shown below:

In column 6, line 54, "'B'" should be -- "b" --.
In column 8, line 9, "'B'" should be -- "b" --.
In claim 1, column 9, line 2, "'B'" should be -- "b" --.
In claim 3, column 10, line 12, "'B'" should be -- "b" --.

Signed and Sealed this

Twentieth Day of May, 1997

BRUCE LEHMAN

Attest:

Attesting Officer

Commissioner of Patents and Trademarks